United States Patent
Parab

(10) Patent No.: US 6,353,029 B1
(45) Date of Patent: Mar. 5, 2002

(54) STORAGE STABLE TRETINOIN AND 4-HYDROXYANISOLE CONTAINING TOPICAL COMPOSITION

(75) Inventor: Prakash V. Parab, Plainsboro, NJ (US)

(73) Assignee: Bristol-Myers Squibb Company, New York, NY (US)

( * ) Notice: Subject to any disclaimer, the term of this patent is extended or adjusted under 35 U.S.C. 154(b) by 0 days.

(21) Appl. No.: 09/644,912

(22) Filed: Aug. 24, 2000

(51) Int. Cl.[7] .................. A61K 31/07; A61K 31/05
(52) U.S. Cl. .......................... 514/725; 514/731
(58) Field of Search ................ 514/559, 725; 1/731

(56) References Cited

U.S. PATENT DOCUMENTS

| | | | |
|---|---|---|---|
| 5,194,247 A | | 3/1993 | Nair et al. |
| 5,326,566 A | * | 7/1994 | Parab |
| 5,420,106 A | * | 5/1995 | Parab |
| 5,470,567 A | | 11/1995 | Nair et al. |
| 5,702,711 A | * | 12/1997 | Parab |
| 5,705,168 A | * | 1/1998 | Parab |
| 5,786,344 A | * | 7/1998 | Ratain et al. |
| 6,008,254 A | | 12/1999 | Kligman et al. |

OTHER PUBLICATIONS

Motto et al., J. Chromat., 48, 1989 pp. 255–262.
British Pharmacopeia, II,1993 p. 1137.
Brisaert et al., Pharma, Acta. Helv., 70,1995 pp. 161–166.

* cited by examiner

Primary Examiner—William R. A. Jarvis
Assistant Examiner—Vickie Kim
(74) Attorney, Agent, or Firm—Maureen P. O'Brien; Charles J. Zeller

(57) ABSTRACT

A long-term storage stable tretinoin and 4-hydroxyanisole composition contains low molecular weight polyethylene glycol, antioxidant, a chelating agent, lower alkanol and water. The chelating agent provides at least two of the functions of oxygen scavaging, free radical chain terminating and reducing. The composition has a pH of 2.5 to 5 and a water content of at least 12%.

13 Claims, No Drawings

STORAGE STABLE TRETINOIN AND 4-HYDROXYANISOLE CONTAINING TOPICAL COMPOSITION

BACKGROUND OF THE INVENTION

Presently, there is no adequate dermatological treatment for hyperpigmentary disorders, such as solar lentigines, melasma and post-inflammatory hyperpigmentation. The depigmentation market is currently serviced by marginally effective prescription and over-the-counter ("OTC") products.

The principal active in OTC products is hydroquinone. It is employed at a level of 1.5% or 2%.

Prescription strength hydroquinone dermatological products contain 3% or 4% hydroquinone. Such products are irritating to the skin and can cause irreversible depigmentation. Thus there is great need for a safe and effective treatment for hyperpigmentary disorders.

Nair et al U.S. Pat. No. 5,194,247, discloses a corticosteroid free synergistic depigmentation composition containing 0.1% to 5%, by weight, 4-hydroxyanisole ("4-HA") and 0 001% to 1%, by weight, of at least one retinoid selected from all-trans retinoic acid, (N-acetyl-4-aminophenyl) retinoate and 11-cis, 13-cis-12-hydroxymethyl retinoic acid-Δ-lactone.

Nair et al U.S. Pat. No. 5,470,567, discloses a corticosteroid free synergistic composition for skin depigmentation. The composition comprises 0. 1% to 2%, by weight, 4-HA and a retinoid. The retinoid is 0.001% to 0.1%, by weight, all-trans retinoic acid; 0.001% to 0.01%, by weight, (N-acetyl-4-aminophenyl) retinoate or 0.001% to 0.1% by weight 11-cis, 13-cis-12-hydroxymethyl retinoic acid-Δ-lactone.

Thus, the prior art appreciates the use of 4-HA and all-trans retinoic acid in treating hyperpigmentary disorders. All-trans retinoic acid is also known as Vitamin A acid and as Tretinoin. It is henceforth referred to herein as "Tretinoin".

U.S. Pat. No. 5,470,567, discloses testing of a solution of 1% 4-HA and 0.01% tretinoin in 98.99% PEG-8/ethanol (5:95) (see Column 6, lines 36–43). The solution was obviously freshly prepared and tested immediately thereafter. Patentees do not teach or even suggest that such solution would provide long term storage stability of tretinoin and 4-HA contained therein.

Assuming that the ethanol employed by patentees was ethanol USP (containing 5% water), patentees' composition containing 98.99% of a 5:95 mixture of PEG-8 and ethanol, respectively, would have contained 4.7% water, an amount insufficient to solubilize other formulation ingredients found necessary by the present inventors to enable long-term storage stability of solutions containing 4-HA and tretinoin.

It should be noted that patentees in U.S. Pat. No. 5,470,567 and 5,194,247 fail to appreciate that 4-HA, in the presence of emulsifiers, degrades tretinoin contained in emulsion formations or that a 4-HA and tretinoin solution containing at least 12%, preferably at least 15%, more preferably at least 20% water, as in the present invention, will afford long-term stability of the tretinoin and 4-HA components.

Kligman et al U.S. Pat. No. 6,008,254 discloses a method of treating skin disorders with high-strength tretinoin. Patentees disclose a composition in which tretinoin is carried in a solvent vehicle. Patentees teach that Tretinoin is substantially insoluble in aqueous vehicles and therefore organic solvent vehicles are preferred. Patentees indicate that a preferred vehicle comprises from about 20 to 80%, by weight, ethanol or isopropanol with the balance being liquid glycol, preferably polyethylene glycol. The Examples illustrate a 0.25%, by weight, solution of tretinoin in a 50:50 mixture of 95% ethanol/polyethylene glycol 400.

SUMMARY OF THE INVENTION

The object of the present invention was to develop a composition comprising a solution of tretinoin and 4-HA having long term physical and chemical stability (viz. long term storage stability), as hereinafter defined, and optimal skin permeation, said composition being useful in the topical treatment of solar lentigines and related hyperpigmented lesions.

Tretinoin is known to be a very unstable drug. It can undergo thermal, oxidative and photo degradation. Because of its instability, the United States Pharmacopoeia allows up to a 35% overage for commercial 0.05% tretinoin solution formulations marketed in the United States. The British Pharmacopoeia allows a 20% overage for tretinoin solution and commercial tretinoin products in Europe are available in 0.025, 0.05, 0.1 and 0.2% strengths.

Compared to tretinoin, 4-HA is more stable, however, it can still undergo oxidative decomposition to hydroquinone and other degradation products.

Oxidation and photochemical reactions are, for the most part, one-electron reactions. Trace amounts of environmental agents can powerfully catalyze these reactions. Contamination by trace metal ions can catalyze oxidative reactions by many orders of magnitude. Even the presence of trace amounts of photosensitive agents in the excipients can cause a susceptible molecule, such as tretinoin, to undergo apparent photochemical reactions.

Oxidative degradation reactions are free radical reactions. Characteristically, many free radical reactions involve lag time or lag phase corresponding to gradual build-up of free radicals via the initial step. If the radicals produced from the initiator go into a propagative cycle, the overall loss of a drug, like tretinoin, will then follow first-order decay with respect to the drug. If chain branching occurs, as it the case of drugs containing conjugated double bonds, the overall loss of drug will be many orders of magnitude and the drug will have a very short shelf life.

Oxidative degradation kinetics involves lag time. Since, oxygen solubility in solvents, such as water and alcohol, is temperature dependent, the interpretation of temperature effects on oxidative reactions is not predictable.

The complications involved in oxidative degradation kinetics make it difficult to rely on accelerated stability data to evaluate the shelf like of tretinoin.

Tretinoin is known to undergo antioxidation. Various degradation products are produced, for example, epoxides, dioxetane, an endoperoxide and double-bond cleavage products. The oxidation process may also result in isomerization (Motto, M. G. et al, J. Chromat., 48, 1989, pages 255–262).

In general, retinoids are known to isomerize by chemical methods, with heat, and, most importantly, by the action of light.

Theoretically, each of the double bonds in retinoic acid can undergo isomerization to give mono, cis, and multiple cis isomers, resulting in a possible total of sixteen double bond isomers. Eight additional isomers are possible due to cyclization of the 7-cis isomer of retinoic acid. Thus a total of twenty four photoisomers is possible.

The chemical stability of 0.05% tretinoin in solution and gel formulations is reported in the literature (see British Pharmacopoeia, II, 1993, page 1137).

The shelf life of tretinoin in a propylene glycol-alcohol solution at 25° C is 6.7 months. In an aqueous tretinoin gel with lauromacragol (Brig® 35s) as the solubilizing agent, the shelf like is twelve days. The shelf life of tretinoin in aqueous gels, with and without Cremophor® RH40 as a solubilizing agent, is 3 months and 10 months respectively. The stability of tretinoin is low in solubilized formulations and is influenced by the types of solubilizing agents and other excipients used in the formulations (Brisaert, M. G., et al, Pharma. Acta. Helv., 70, 1995, pages 161–166).

In an effort to develop a pharmaceutically elegant dermatological composition containing tretinoin and 4-HA and having long term storage stability (as hereinafter defined), the present inventors incorporated the tretinoin and 4-HA in cream compositions. The oil-in-water emulsion based creams broke. Most likely, this was due to the 4-HA component as it is soluble in both the oil phase and water phase. Addition of other emulsifiers and thickeners resolved the problem of physical instability of the emulsion; however, tretinoin proved to be very unstable in such formulations.

DESCRIPTION OF THE PREFERRED EMBODIMENT OF THE INVENTION

The long-term storage stable composition of the present invention comprises:

(a) 0.5 to 5% (w/v), preferably 1 to 3% (w/v), more preferably about 2% (w/v) 4-HA;

(b) 0.002 to 0.05% (w/v), preferably 0.005 to 0.02% (w/v), more preferably 0.01% (w/v) tretinoin;

(c) 2 to 10% (v/v), preferably 3 to 5% (v/v), more preferably about 4% (v/v) of a low molecular weight liquid polyethylene glycol, most preferably, PEG-8;

(d) 0.001 to 1.5% (w/v), preferably 0.003 to 1.25% (w/v), more preferably about 1% (w/v) of an antioxidant or mixture of antioxidants selected from the group consisting of butylated hydroxyanisole ("BHA"), butylated hydroxytoluene ("BHT"), ascorbic acid, ascorbyl palmitate, lecithin, norhydroguaiaretic acid, propyl gallate, a-tocopherol, sodium bisulfite, cysteine, sodium metabisulfite, thioglycerol, thioglycolic acid, and thiomersal; preferably BHT, ascorbic acid, ascorbyl palmitate and mixtures thereof; the antioxidant or mixture of antioxidants being selected so as to provide at least two of the finctions of oxygen scavenging, chain terminating and reducing;

(e) 0.001 to 0.1% (w/v), preferably 0.002 to 0.05% (w/v), more preferably 0.003 to 0.02% (w/v), most preferably about 0.015% (w/v), of a chelating agent selected from the group consisting of citric acid, disodium ethylenediamine tetraacetic acid ("Disodium EDTA"), phosphoric acid, tartaric acid, sorbitol, phenylalanine and mixtures thereof, preferably, citric acid, disodium EDTA and mixtures thereof;

(f) 50 to 88% (v/v), preferably 60 to 85% (v/v), more preferably 65 to 80% (v/v), most preferably, 75 to 80% (v/v), of lower alkanol, preferably isopropanol, ethanol or a mixture thereof, more preferably ethyl alcohol (USP);

(g) an acidulant in an amount sufficient to adjust the pH of the composition to from about 2.5 to about 5, preferably about 3 to about 4.5, more preferably about 4; and (h) water qs to 100%.

The water content of the composition of the present invention is critical. Water is necessary to dissolve the chelating agent(s) present in the composition. Water also acts as a moisturizer. Deionized or purified water is preferred.

The amount of water present in the composition must be sufficient to dissolve the chelating agent(s) present in the composition. The composition preferably contains at least 12% water, more preferably, at least 15% water, most preferably at least 20% water.

The chelating agent is an essential component of the composition of the invention as it is necessary to the stability of the tretinoin component.

Any pharmaceutically acceptable acid can be employed as the acidulant, for example, hydrochloric acid, phosphoric acid and citric acid. Citric acid and phosphoric acid are preferred as they also finction as chelating agents. Thus, when citric acid, phosphoric acid or a mixture of citric acid and phosphoric acid is employed as a chelating agent in the composition of the invention, the need for an acidulant may be obviated.

The antioxidant is another essential component of the composition of the invention. The term"antioxidant" is understood by those skilled in the art as encompassing the finctions of reducing, free radical chain terminating and oxygen scavenging. With this in mind, the antioxidant employed in the composition of the present invention is selected from the group consisting of butylated hydroxyanisole ("BHA"), butylated hydroxytoluene ("BHT"), ascorbic acid, ascorbyl palmitate, lecithin, norhydroguaiaretic acid, propyl gallate, a-tocopherol, sodium bisulfite, cysteine, sodium metabisulfite, thioglycerol, thioglycolic acid and thiomersal.

It should be understood that the selection of the antioxidant from the aforementioned group must satisfy the requirement that at least two of the functions of oxygen scavenging, free radical chain terminating and reducing are provided. Preferably the two functions that are provided are oxygen scavenging and free radical chain terminating. Thus, BHT, ascorbic acid, ascorbyl palmitate and mixtures thereof are preferred antioxidants.

The following Example is provided to illustrate the invention and not in limitation thereof.

EXAMPLE 1

| Ingredients | |
|---|---|
| 4-Hydroxyanisole* | 2.00% (w/v) |
| Tretinoin** | 0.01% (wlv) |
| Ethyl alcohol (USP)*** | 77.80% (v/v) |
| PEG-8 | 3.90% (v/v) |
| BHT | 0.088% (w/v) |
| Ascorbic acid | 0.044% (w/v) |
| Citric acid | 0.0088% (w/v) |
| Ascorbyl palmitate | 0.0044% (w/v) |
| Disodium EDTA | 0.0044% (w/v) |
| Water | 18.50% (v/v) |

*a 2.5% overage should be employed
**a 20% overage should be employed
***a 2% overage should be employed The composition is prepared as follows:

The disodium EDTA is added to the water and rapidly agitated until dissolved.

The citric acid, ascorbic acid, ascorbyl palmitate, BHT and Tretinoin are added to the ethyl alcohol under agitation until all solids are dissolved.

The 4-HA is slowly added to the ethyl alcohol solution under agitation.

When the 4-HA is dissolved in the ethyl alcohol solution, the sodium EDTA/water solution is slowly added and agitation is continued until all solids are dissolved.

During manufacture, the position, depth and mixing speed of the propeller are adjusted to minimize aeration of the solution.

Most desirably the process is carried out under yellow light and under a nitrogen blanket.

Regression analysis of room temperature data for a solution in accordance with the present invention, having a 25% average of tretinoin and a minimum specification of 90%, showed a 95% confidence limit that was within specifications through at least 24 months. Extrapolation of the room temperature regression analysis data with a 25% tretinoin overage also showed that a 20% overage of tretinoin would be sufficient to merit at least a 24-month expiration period with a lower limit of 90%. Thus, a 20% overage is recommended for the solution of Example 1.

A 2.5% overage of 4-HA is also recommended.

It is also desirable that a 2% overage of ethyl alcohol be employed to allow for loss during manufacture and filling.

Since oxidation of tretinoin can substantially be prevented by excluding oxygen from the composition of the invention, the following measures should be taken to protect tretinoin during manufacture, filling and storage of the composition of the invention.

During the manufacturing operation, mixing speed should be optimized to minimize aeration.

Oxygen scavengers, such as ascorbic acid and ascorbyl palmitate should be incorporated in the composition. A reducing agent should also be incorporated in the composition to reduce any tretinoin that oxidizes during processing. Ascorbic acid is preferred as it functions as an oxygen scavenger and as a reducing agent.

Ionizable molecules are more readily oxidatively degraded in the ionized form than in the nonionized form. Moreover, oxidative degradation of same can be minimized by lowering the pH of the composition. Therefore, it is desirably that an acidulant be incorporated in the formulation to reduce the composition's pH. Citric acid is a preferred acidulant, since it also acts as a chelating agent.

Most desirably, at least one chelating agent should be incorporated in the composition of the invention. The chelating agent chelates with metal contaminants which may come form excipients, packaging and during processing and filing. Disodium ethylenediamine tetraacetic acid and citric acid are preferred chelating agents. Citric acid is particularly preferred as it also finctions to reduce the pH of the composition.

It is also desirable that the composition of the invention contain a free radical chain terminator, such as butylated hydroxytoluene ("BHT") to protect the tretinoin and 4-HA over the product's shelf life.

Since tretinoin is susceptible to photo degradation the manufacturing and filling operations are preferably carried out under yellow light.

The composition of the present invention contains a high concentration of ethyl alcohol. Solid state 4-HA can create a static charge when added to alcoholic solution. To avoid the potential for explosion during manufacture an inert gas, such as nitrogen or argon, is preferably used to blanket the mixing tank.

To insure that the tretinoin, in the composition of the invention, remains within 90% of label strength for at least two years, it is desirable that an overage of 20 to 25% tretinoin be employed.

The composition of the present invention was found to be incompatible with plastics such as acrylonitrile butadiene styrene copolymer ("ABS").

The container closure system utilized to package the composition of this invention clearly has an impact on tretinoin photodegradation. Photostability studies, carried out under high intensity light, with different packaging configurations showed that a blue, opaque high density polyethylene bottle, provided with a polypropylene cap, that is preferably blue, and that is stored in a carton, preferably a paperboard carton, provided the best protection of tretinoin from photodegradation during storage.

Most desirably the bottle is fitted with an applicator, preferably a PVC foam deer-foot applicator. Preferably, the applicator is mounted on a polyoxymethylene rod, which allows application of the composition of the invention to both small and large solar lentigines lesions with minimal application to normal surrounding skin. This packaging design provides hands-off delivery of the medication. The goal of treatment with the composition of the invention is to depigment the hyperpigmented lesion to a level equal to that of the normal surrounding skin. Application of the composition of the invention to normal skin could produce a"halo" effect. Use of an applicator, such as the PVC foam deer-foot applicator, keeps the amount of product contacting normal skin to a minimum thereby substantially avoiding the undesirable"halo" effect.

Preferably, the orifice of the high density polyethylene bottle is fitted with a wiper, preferably made of low-density polyethylene. The wiper serves to wipe excess solution from the rod and applicator tip.

As noted earlier, the present composition differs from the prior art solution of Nair et al U.S. Pat. Nos. 5,194,247 and 5,470,567 in that Nair et al's solution was clearly made up immediately prior to use, was not intended for long term storage and would not provide long term storage stability of the Tretinoin component.

The concentration of water is critical to long term storage stability of tretinoin in the composition of the present invention. The 4-HA and tretinoin containing composition of the invention must have at least 12% (v/v) water, preferably at least 15% (v/v), more preferably at least 20% (v/v) water.

It should be noted that as used herein, and in the claims that follow, "long term storage stability" means that when stored at an elevated temperature of 40° C. for twelve weeks the concentration of tretinoin in the composition is at least 85%, preferably at least 90%, of the initial concentration, and when stored at room temperature (25° C.) for two years, the concentration of tretinoin in the composition is at least 90% of the initial concentration.

It should also be noted that, unless indicated to the contrary herein, all percentages are based on the total volume of the composition.

What is claimed is:

1. A topical solution having long term storage stability comprising:
   (a) about 0.5 to about 5% w/v 4-hydroxyanisole (HA);
   (b) about 0.002 to about 0.05% w/v Tretinoin;
   (c) about 2 to about 10% v/v of a liquid low molecular weight polyethylene glycol;
   (d) about 0.001 to about 1.5% w/v of an antioxidant or mixture of antioxidants, the antioxidant or mixture of antioxidants being selected such that at least two of the finctions of oxygen scavaging, free radical chain terminating, and reducing, are provided;

(e) about 0.001 to about 0.1% w/v of a chelating agent;

(f) about 50 to about 88% v/v of a lower alkanol; and (g) water qs to 100%;

said solution having a pH of about 2.5 to about 5 and a water content of at least 12% v/v.

2. The solution as claimed in claim 1, wherein the 4-HA is present in an amount of about 1 to about 3% w/v; the tretinoin is present in an amount of about 0.005 to about 0.02% w/v, the liquid low molecular weight polyethylene glycol is present in an amount of about 3 to about 5% v/v; the antioxidant is present in an amount of about 0.003 to about 1.25% w/v; the chelating agent is present in an amount of about 0.002 to about 0.05% w/v; and the lower alkanol is present in an amount of about 60 to about 85% v/v.

3. The solution as claimed in claim 1, wherein the 4-HA is present in an amount of about 2% w/v; the tretinoin is present in an amount of about 0.01% w/v; the liquid low molecular weight polyethylene glycol is present in an amount of about 4% v/v; the antioxidant is present in an amount of about 1% w/v; the chelating agent is present in an amount of about 0.003 to about 0.02% w/v; and the lower alkanol is present in an amount of about 65 to about 80% v/v.

4. The solution of claim 1, wherein the antioxidant or mixture of antioxidants is selected from the group consisting of BHA, BHT, ascorbic acid, ascorbyl palmitate, lecithin, norhydroguaiaretic acid, propyl gallate, α-tocopherol, sodium bisulfite, cysteine, sodium metabisulfite, thioglycerol, thioglycolic acid and thiomersal.

5. The solution of claim 4, wherein the chelating agent is selected from the group consisting of citric acid, disodium EDTA, phosphoric acid, tartaric acid, sorbitol, phenylalanine and mixtures thereof.

6. The solution as claimed in claim 1, wherein the water content is at least 15% v/v.

7. The solution as claimed in claim 1, wherein, the water content is at least 20% v/v.

8. The solution as claimed in claim 1, wherein the pH is about 3 to about 4.5.

9. The solution as claimed in claim 1, wherein the pH is about 4.

10. The solution as claimed in claim 1, wherein the two functions provided are oxygen scavenging and free radical chain terminating.

11. The solution as claimed in claim 4 wherein the polyethylene glycol is PEG-8; the antioxidant or mixture of antioxidants is BHT, ascorbic acid, ascorbyl palmitate or a mixture thereof; the lower alkanol is ethanol, isopropyl alcohol or a mixture thereof; and the chelating agent is citric acid, disodium EDTA or a mixture thereof.

12. The solution as claimed in claim 5, further including an amount of an acidulant sufficient to adjust the pH of the solution to said pH of about 2.5 to about 5.

13. The solution as claimed in claim 5, comprising 2% w/v 4-HA; 0.01% w/v tretinoin; 77.8% v/v ethyl alcohol USP; 3.9% v/v PEG-8; 0.088% w/v BHT; 0.044% w/v ascorbic acid; 0.0088% w/v citric acid; 0.0044% w/v ascorbyl palmitate; 0.0044% w/v disodium EDTA and 18.5% water.

* * * * *